(12) United States Patent
Zeligs et al.

(10) Patent No.: US 6,416,793 B1
(45) Date of Patent: Jul. 9, 2002

(54) FORMULATIONS AND USE OF CONTROLLED-RELEASE INDOLE ALKALOIDS

(75) Inventors: Michael A. Zeligs, Boulder, CO (US); Irwin C. Jacobs, Eureka, MO (US)

(73) Assignee: BioResponse, L.L.C., Boulder, CO (US)

(*) Notice: Subject to any disclaimer, the term of this patent is extended or adjusted under 35 U.S.C. 154(b) by 0 days.

(21) Appl. No.: 09/614,007

(22) Filed: Jul. 11, 2000

(51) Int. Cl.[7] .......................... A61K 35/78; A61K 9/14; A61K 9/16; A61K 9/50
(52) U.S. Cl. ...................... 424/725; 424/775; 424/489; 424/490; 424/492
(58) Field of Search ................................. 424/725, 775, 424/489, 490, 492

(56) References Cited

U.S. PATENT DOCUMENTS

| | | |
|---|---|---|
| 4,588,724 A | 5/1986 | Greenway et al. |
| 6,086,915 A | 7/2000 | Zeligs |
| 6,165,500 A * | 12/2000 | Cevc |

OTHER PUBLICATIONS

Berlan et al., 1991, "Anorectic Effect of Alpha$_2$–Antagonists in Dog: Effect of Acute and Chronic Treatment," *Pharmacology Biochemistry & Behavior* 39:313–320.
Berlin et al., 1986, "Absence D'efficacité de la Yohimbine dans le Traitement de l'Obésité," *J. Pharmacol.* (Paris) 17(3):343–347.
Berlin et al., 1989, "The alpha–2 adrenoceptor antagonist yohimbine does not facilitate weight loss but blocks adrenaline induced platelet aggregation in obese subjects," *Therapie* 44(4)301.
Carelli et al., 1998, "Effects of vehicles on yohimbine permeation across excised hairless mouse skin," *Pharmaceutica Acta Helvetiae* 73:127–134.
Charney et al., 1982, "Assessment of $\alpha_2$ Adrenergic Autoreceptor Function in Humans: Effects of Oral Yohimbine," *Life Sciences* 30(23):2033–2041.
Curtis–Prior et al., 1984, "Application of Agents Active at the $\alpha_2$ –Adrenoceptor of Fat Cells to the Treatment of Obesity –A Critical Appraisal," *International Journal of Obesity* 8(1)201–213.
Dulloo et al., 1999, "Efficacy of a green tea extract rich in catechin polyphenols and caffeine in increasing 24–h energy expenditure and fat oxidation in humans," *Am. J. Clin. Nutr.* 70:1040–5.
Guthrie et al., 1990, "Yohimbine bioavailability in humans," *Eur. J. Clin. Pharmacol.* 39(4):401–411.
Kao et al., 2000, "Modulation of Endocrine Systems and Food Intake by Green Tea Epigallocatechin Gallate," *Endocrinology* 141(3):980–987.
Kucio et al., 1991, "Does Yohimbine Act As A Slimming Drug?," *Israel J. Med. Sci.* 27(10):550–556.
Le Corre et al., 1997, "Cerebrospinal fluid and plasma disposition of yohimbine and 11–hydroxy–yohimbine in young and older healthy subjects, and Alzheimer's disease patients," *Eur. J. Clin. Pharmacol.* 52: 135–138.
Le Verge et al., 1992, "Determination of yohimbine and its two hydroxylated metabolites in humans by high–performance liquid chromatography and mass spectral analysis," *Journal of Chromatography* 574:283–292.
Sax, 1992, "Yohimbine does not affect fat distribution in men," *International Journal of Obesity* 15:561–565.
Berlan et al., 1991, "Plasma catecholamine levels and lipid mobilization induced by yohimbine in obese and non obese women," *International Journal of Obesity* 15:305–315.
Grasing et al., 1996, "Effects of Yohimbine on Autonomic Measures are Determined by Individual Values for Area Under the Concentration –Time Curve," *J. Clin. Pharmacol.* 36:814–822.
Le Corre et al., 1999, "Biopharmaceutics and metabolism of yohimbine in humans," *European Journal of Pharmaceutical Sciences* 9:79–84.
Mash et al., "Medication Development of Ibogaine as a Pharmacotherapy for Drug Dependence," *Annals New York Academy of Sciences* 274–292.
Zahorska–Markiewicz et al., 1986, "Adrenergic Control of Lipolysis and Metabolic Responses in Obesity," *Horm. metabol. Res.* 18:693–697.

* cited by examiner

*Primary Examiner*—Francisco Prats
*Assistant Examiner*—Susan D. Coe
(74) *Attorney, Agent, or Firm*—Pennie & Edmonds LLP

(57) ABSTRACT

The present invention relates to spray dried hydrophobic phytochemical (i.e., yohimbine and ibogaine) compositions, a process for making such compositions and a method of using such compositions for, e.g., the promotion of weight loss. Typically, the hydrophobic dietary compositions of the present invention exhibit enhanced absorptivity when taken orally.

10 Claims, No Drawings

FORMULATIONS AND USE OF CONTROLLED-RELEASE INDOLE ALKALOIDS

1. DESCRIPTION OF THE FIELD

This invention relates to the use of a new formulation of indole phytochemicals to promote their absorption. In particular, the phytochemicals suitable for use according to the present invention are the indoles found in extracts of the bark of *Pausinystalia yohimbe* (yohimbine, corynanthine and rauwolscine) and ibogaine, a chemical derived from the rain forest shrub *Tabernanthe iboga*. The compositions of the invention may be formulated starting from the natural material in which the indole phytochemical is naturally found (i.e., bark or bark extracts) or from the pure dietary indoles themselves. Preparations of such phytochemicals are described which promote improved absorption of insoluble dietary substances and promote the effects of said phytochemicals. This facilitated absorption of poorly soluble dietary substances amplifies the useful dietary influences of such substances.

2. BACKGROUND OF THE INVENTION

Some phytochemicals found in edible plants have importance in health promotion due to activity which promotes improved fat metabolism. This activity results from support for the action of catecholamine hormones which trigger the release of stored fatty acids from fat cells.

Yohimbine is a dietary indole and one of a family of stereoisomers (i.e., yohimbine, corynanthine and rauwolscine) found in extracts from the bark of *Pausinystalia yohimbe*. This group of compounds posses a number of uses as modulators of catecholamine hormone action. Apart from possible medical uses as an anti-depressant, as a therapy for male impotence, and to promote salivation, an important application of yohimbe alkaloids is as a means of inducing mobilization of stored fat through blocking the action of catecholamines at α-adrenergic receptors. Blocking the α2-adrenergic receptors on the surface of fat cells (adipocytes) results in greater influence of competing β-adrenergic receptors promoting more active breakdown and release of stored triglycerides. This causes the release of non-esterified free fatty acids into the general circulation for use as a metabolic energy source during dieting and exercise (Lafontan and Betuing, "Regulation of Fat-Cell Function by α-2 Adrenergic Receptors," Advances in Pharmacology, 42, 496–8 (1998)). This peripheral action of yohimbe alkaloids combines with a separate central nervous system activity and the subsequent α adrenergic blocking results in suppression of appetite. Together these actions make *Pausinystalia yohimbe* alkaloids desirable as compounds to facilitate weight loss in overweight and obese individuals.

Currently, many weight-loss promoting dietary supplements use "catecholamine-mimics" from natural sources like Ma Huang, containing ephedrine, and Bitter Orange Extract (Citrus Aurantium), containing synephrine. Both the endogenously produced catecholamine hormones, norepinephrine and epinephrine, and the natural product "catecholamine-mimics" have been shown to promote the release of stored fatty acids during reduced calorie diets and sustained exercise. However, this use of ephedrine, synephrine, and other catecholamine related drugs like amphetamine and phenylpropanolamine is plagued by a host of side effects and risks. These side effects include excess catecholamine-like activity and result in tremor, sleeplessness, and uncontrolled high blood pressure in susceptible individuals.

Unlike direct acting catecholamines and related natural products, yohimbine is an indole alkaloid which acts indirectly to induce the release and more efficient action of catecholamines already present in the central and peripheral nervous system. Yohimbine has been demonstrated to both increase circulating levels of norepinephrine (Berlan, et al., "Plasma Catecholamine Levels and Lipid Mobilization Induced by Yohimbine in Obese and Non-Obese Women," International Journal of Obesity, 15, 305–15 (1991)), and to promote fat loss during calory restricted dieting (Zahorska-Markiewicz, et al., "Adrenergic Control of Lipolysis and Metabolic Responses in Obesity," Hormone Metabol. Res., 18, 693–7 (1986)). Yohimbine acts by increasing circulating norepinephrine, which activates β-adrenergic receptors on fat cells, and by directly occupying and blocking α-adrenergic receptors. These combined effects, i.e., supporting norepinephrine release and blocking the specific inhibition of norepinephrine mediated mobilization of stored fat, promotes a more efficient release of stored fatty acids. This can promote more rapid weight loss during a program of reduced food intake and low intensity exercise.

Yohimbine, however, demonstrates poor absorption when taken orally without special formulation. The low solubility and poor absorption of the yohimbe family of indoles has been demonstrated through pharmacokinetic study of yohimbine and rauwolscine. When administered, yohimbine and rauwolscine have only brief and variable plasma half lives (0.5 to 1 hour) and a limited bioavailability of less than 30% (Guthrie, et al., "Yohimbine Bioavailability in Humans," European J Clin Pharmacol, 39, 409–11 (1990)). Instead of the brief and unpredictable peak which follows ingestion of unformulated yohimbe extract or isolated yohimbine, a prolonged low level of circulating yohimbine and its active metabolites is a more desirable and safer approach to facilitate weight loss (Le Corre, P. Dollo, G, et al. "Biopharmaceutics and Metabolism of Yohimbine in Humans," Eur J. Pham Sci, 9(1): 79–84 (1999)). The processing of natural yohimbe extract to provide more complete, more sustained, and more controlled absorption is needed. Modifying the absorption of active indoles from yohimbe extract would provide a dietary supplement which limits peak blood levels to more safely promote lipolysis through peripheral α adrenergic blocking activity. The unique central action of yohimbine and its metabolites to increase circulating levels of norepinephrine and therefore, to curb appetite, would be reduced but still present and prolonged.

As a result, a need exists to increase the absorption and prolong the bioavailability of yohimbine and other similar alkaloids from *Pausinystalia yohimbe*. Formulations of indoles which promote more complete absorption and more sustained release into the circulation can be used to increase the effectiveness of these substances. Processing these phytochemicals for better absorption will also provide for their use in promoting weight loss at a lower oral dose. Further, since side effects from yohimbine relate to peak blood levels and cross over into the central nervous system, formulations for controlled release are also safer. Regulated and sustained absorption of yohimbe alkaloids will increase their usefulness in promoting weight loss which requires persistent, low levels to support the greatest cumulative release of stored fat.

The improved absorption of cruciferous indoles, particularly diindolylmethane (DIM) and related indoles from the precursor phytochemical, glucobrassicin, has been the subject of a United States patent application (U.S. patent application Ser. No. 09/053,180, filed on Apr. 1, 1998). The objective of this patent was to provide significant absorption of DIM and other poorly soluble hydrophobic natural products which were not absorbed sufficiently without processing. This contrasts with the present invention in which the objective of processing is to modify the pattern of absorption of alkaloids in *Pausinystalia yohimbe* bark extracts, *Tabernanthe iboga* extracts, purified yohimbine, purified ibogaine, purified yohimbine and purified corynanthine, for improved safety and controlled release. In particular, processing methods for yohimbe extract eliminates a brief, potentially toxic, early peak and introduces sustained, controlled-release of yohimbine alkaloids for a period of hours.

Other applications of formulated DIM are the subject of separate United States patent applications detailing methods and formulations for promoting weight loss (U.S. patent application Ser. No. 09/404,112, filed on Sep. 23, 1999) and for use in the treatment of recurrent mastalgia and endometriosis (U.S. patent application Ser. No. 09/404,111, filed on Sep. 23, 1999). Absorption of pure yohimbine for delivery through the skin to promote regional fat loss has been the subject of a United States patent (U.S. Pat. No. 4,588,724). Separate study of yohimbine formulations has sought to identify formulations that would provide better transdermal absorption through genital skin for the treatment of erectile dysfunction in men (Carell, et al., "Effect of Vehicles on Yohimbine Permeation Across Excised Hairless Mouse Skin," Pharmaceutica Acta Helvetiae, 73, 127–34 (1998)).

Two previous patent applications relate to the combined use of pure, unprocessed yohimbine alkaloids in combination with other substances. The first patent (U.S. Pat. No. 5,492,907) relates to the use of yohimbine as one of many a receptor antagonists used in combination with a dopamine receptor antagonist for treating schizophrenia. The second patent (International Patent Publication no. WO9903364A1, "Nutritional Composition for Subjects Under Stress") relates to the use of unprocessed yohimbine in combination with carnitine, gurana, lecithin and malic acid as a nutritional composition for individuals debilitated by stress.

3. SUMMARY OF THE INVENTION

Specialized nutrient preparations and formulation techniques using plant-based compounds have been developed for use as dietary supplements. These preparations provide for efficient and sustained administration of the formulated dietary indoles. The present invention claims new formulations of indoles created through the processing of extracts from *Pausinystalia yohimbe* bark, the processing of extracts from *Tabernanthe iboga* and the processing of the purified chemicals yohimbine and ibogaine, corynanthine, and rauwolscine. These formulations result in absorption enhancing activity to provide greater and more sustained gastrointestinal absorption of the formulated compounds, including *Pausinystalia yohimbe* indole alkaloids. The formulations specified allow for new uses of *Pausinystalia yohimbe* bark extracts, *Tabernanthe iboga* extracts, purified yohimbine, ibogaine, corynanthine, and rauwolscine, including more effective use in dietary supplement compositions used to promote weight loss. It is another object of the present invention to provide compositions comprising one or more of *Pausinystalia yohimbe* bark extracts, *Tabernanthe iboga* extracts, purified yohimbine, corynanthine, rauwolscine and/or purified ibogaine, either formulated according to the present invention or not, combined with epigallocatechin gallate (EGCG) found in green tea, which prolongs the action of circulating norepinephrine. Surprisingly, the effects of EGCG and the one or more of *Pausinystalia yohimbe* bark extracts, purified yohimbine, ibogaine, corynanthine and/or rauwolscine are synergistic to one another.

New formulation technology has been developed which permits the creation of a microdispersion of insoluble dietary substances in association with polyethylene glycol esters and natural surfactants. This microdispersion is captured within particles of starch through a spray-drying process. The result is a fine powder, with each particle containing microparticles of the solidified dietary substance in amorphous, non-crystalline complexes. The preparation stabilizes the dietary substance, providing a long shelf-life and the ability to combine with other dietary supplement ingredients. Most importantly these preparations enhance the absorption of insoluble dietary substances when ingested, providing for effective treatment with a low dose for long-term users.

4. DETAILED DESCRIPTION OF THE INVENTION

The present invention concerns the formulation and use of nutrient preparations for enhanced absorption of highly insoluble, hydrophobic phytochemicals, including *Pausinystalia yohimbe* bark extracts, *Tabernanthe iboga* extracts, purified yohimbine, ibogaine, corynanthine, and rauwolscine. Among the objectives of the invention is to promote weight loss through the use of such novel formulations. Preparations are based on the steps of co-dissolving the dietary substances in an appropriate solvent, an emulsifier (e.g., vitamin E succinate PEG ester) and phospholipids, followed by the creation of a stable microdispersion in water-soluble matrix-forming agent. Amorphous complexes of microdispersed dietary substances are then co-precipitated within carrier particles formed by spray drying. These formulations, with active dietary substances residing in microparticles, promote enhanced absorption when dissolved and emulsified within the small intestine of a human or animal.

The present invention concerns the formulation and use of extracts from the bark of *Pausinystalia yohimbe, Tabernanthe iboga*, as well as isolated indole alkaloids such as ibogaine, yohimbine, corynanthine, and rauwolscine. The process of formulation described reduces potentially toxic initial plasma level peaks of unprocessed compounds and extracts and promotes enhanced bioavailability and controlled release of active alkaloids. When used with *Pausinystalia yohirabe* bark extracts, this action applies to all of the closely related yohimbine isomers. The formulation processing of the present invention thus has the potential of increasing the safety of *Pausinystalia yohimbe* bark extracts, *Tabernanthe iboga* extracts, purified yohimbine and purified ibogaine, purified corynanthine and purified rauwolscine by avoiding greater central nervous system uptake associated with unwanted autonomic nervous system effects on blood pressure, heart rate and mood in susceptible individuals (Grassing, K, et al., "Effects of Yohimbine von Autonomic Measures Are Determined by Individual Values for Area under the Concentration-time Curve," J Clin Pharmacol, 36, 814–22 (1996)). The objective of the invention is to optimize the use of *Pausinystalia yohimbe* alkaloids and *Tabernanthe iboga* alkaloids alone and in combination with other natural substances to, in the case of yohimbine, facilitate weight loss and for other established uses of yohimbine or iboga alkaloids.

The compositions of the invention comprising *Pausinystalia yohimbe* bark extracts, purified yohimbine, purified corynanthine and purified rauwolscine can be administered to subjects in need thereof for the promotion of weight loss. For effective treatment, the preparation of the invention is administered to a mammal in an approximate dose of from 0.2 to 10 mg/kg/day by oral administration. This administration is effective in promoting the mobilization of stored fat, especially during dietary carbohydrate restriction.

In one embodiment, the method further comprises, in addition to the administration of phytochemical, limiting the subject's carbohydrate intake. In preferred embodiments, the subject's carbohydrate intake is limited to 50, 100, 150, 200, 250, 300, 350, 400, 450 and 500 mg per day.

In a preferred embodiment, the subject to be treated, even though limiting carbohydrate intake, has become resistant to losing weight through limiting of carbohydrate intake alone. In another embodiment, the subject is one who is already on a diet of limited carbohydrate intake. For such a subject, the method of the invention comprises the administration of phytochemical as described herein without additional limitation of carbohydrate intake.

The phytochemicals of the invention may be administered in any appropriate amount in any suitable galenic formulation and following any regime of administration. Preferably, administration is oral.

The actual administered amount of phytochemical, and the amount of daily carbohydrate intake may be decided by a supervising physician and may depend on multiple factors, such as, the age, condition, file history, etc., of the patient in question.

The subject, or patient, to be treated using the methods of the invention is an animal, e.g., a mammal, and is preferably human, and can be a fetus, child, or adult. In a preferred embodiment, the subject is a dog.

Through the discovery of specialized steps involving choice and application of particular solvents, a standardized preparation of Yohimbe bark extract with enhanced absorption and sustained, controlled-release characteristics has been produced. Preliminary study of pure yohimbine revealed it to be in the category of poorly soluble substances with low oral bioavailablity. The ratio of the solubility of yohimbine base in octanol to its solubility in water was studied using UV spectrophotometry. The log P expressing the greater solubility of yohimbine in lipid as compared to in water was found to be 3.17. Thus the solubility of yohimbine, and closely related corynanthine and rauwolscine, is greater in lipid than water media. These compounds can be formulated according to the methods of the invention to enhance their absorption through barriers to fat absorption in the small intestine.

The formulation technology developed is identified by processing steps which allow for the re-distribution of insoluble ingredients to surfactant-rich microparticles. The focus of this processing has been the creation of a solid dispersion of microparticulates contained within a larger matrix of starch particles. These 10 micron starch particles contain the microparticulates which consist of an amorphous solid phase of a mixture of hydrophobic phytochemicals such as yohimbine together with solubilizing emulsifier (e.g., vitamin E succinate polyethylene glycol 1000; vitamin E succinate Polyethylene glycols with polyethylene glycol (with a molecular weight range of 400–2000); other polyethylene glycol esters such as those formed by fatty acids such as oleic acid or stearic acid; polyvinylpyrrolidones; polyvinylpolypyrrolidones; Poloxamer 188, Tweens; or Spans) and a phospholipid.

The formulation process described employs a new approach to particle size reduction through formation of an optimized microdispersion in an aqueous phase which is then converted, through spray drying, to a free flowing powder comprising the water soluble matrix containing the embedded microparticles. In the process, the solubility enhancing activity of polyethylene glycol esters is adapted for maximal dissolution of phytochemical in a warm (from 30° C. to 90° C.) mixture of food-compatible solvents, phospholipid and TPGS.

Possible solvents include hexanol, ethanol, butanol, heptanol, 2-methyl-1-pentanol, various ketone solvents that would be acceptable in foods such as methyl ethyl ketone, acetone and others, propylene glycol and certain ester solvents such as ethyl acetate.

The solubility of a yohimbe bark extract (Kaden Biochemicals, Hamburg, Germany) was studied in a number of food grade solvents. It was found that solvents such as ethyl acetate or n-propyl acetate could solubilize yohimbine but would not extract resinous materials form the bark. Therefore, n-propyl acetate and ethyl acetate are preferred solvents suitable for the methods of the invention for solubilization and extraction of yohimbine, corynanthine, and rauwolscine from yohimbe bark extract. In general, preferred suitable solvents are those solvents that do not result in undesirable extraction of resinous materials from the extract, and are thus compatible with subsequent spray drying and dry particle formation. Such solvents will be apparent to those of skill in the art, as it is easy to determine whether an extract produced from any given solvent is suitable for the methods of the present invention. For example, the solvents hexanol, ethanol, butanol, heptanol, and 2-methyl-1-pentanol are to be avoided since they result in undesirable extraction of resinous material in addition to the desired indole alkaloids, and extracts of yohimbe bark produced with such solvents are generally unsuitable for subsequent spray drying due to the presence of the resinous material.

The choice of a solvent for pure compounds (i.e., not extracts or bark extracts) is less critical, as most solvents capable of dissolving the compound are suitable. Pure ibogaine, yohimbine, corynanthine, and rauwolscine are commercially available from, for example, Sigma Chemicals, St. Louis (yohimbine, Product no. Y3125; corynanthine, Product no. C3380; zrauwolscine, Product no. R104' and ibogaine, Product no. I7003, 2000–2001 Sigma Catalog).

Possible phospholipids can include the constituents of lecithins (e.g., phosphatidyl serine, phosphatidyl inositol and phosphatidyl glycerol); phospholipid derived from soy; phospholipid derived from milk-fat globule membrane "MFGM"; dioleoyl phosphatidylcholine; phoshatidylglycerol; dioleoylphosphatidylglycerol; dimyristoylphosphatidylcholine; dipalmitoylphosphatidylcholine; phosphatidylethalolamines; phosphatidylserines; sphingomyelins; poly gylcerol esters; or ethoxylated castor oil. The phospholipid is added to the TPGS/solvent mixture to cause reduction in size of the dispersed phase after mixing with water. High shear mixing of this organic phase causes either dissolution, or the production of an extremely fine suspension of the phytochemical, or mixture of phytochemicals in an intimate mixture with the solubilizing emulsifier (e.g., TPGS) and phospholipid.

The ratio of the mixtures were refined to maximize the stability of the emulsion. The ratio of TPGS to phytochemical should be in the range of 0.5:1 to 1.5:1. A ratio of 1:1 is preferred. When the phytochemical or phytochemicals are present in an extract, the relevant ratio is the mass of TPGS to the mass of phytochemical present in the extract, not the mass of TPGS to mass of the total extract. The starch should be from 25% to 75% of the total mass of components and is preferably in a ratio of 0.8:1 to 8:1 with the TPGS. The emulsifiers, which can include either or both phosphatidyl choline and bile salts (e.g., sodium cholate, deoxycholate, taurocholate, etc.) should be from 1% to 20% of the total mass, with 5% to 10% preferred. The solvent should be at a mass ratio of 0.5:1 to 8:1 with the active ingredient.

Next this "melt" of extracted hydrophobic components is homogenized in a water based solution of starch or other encapsulator (e.g., modified starch such as Capsul™ Starch from National Starch, Inc.; methylcellulose; hydroxypropyl methylcellulose; hydroxyethylcellulose; hydroxypropyleth-ylcellulose; pectin; gum arabic; gelatin; or other polymeric matrix-forming preparation known to those skilled in the art, soluble in water and, suitable for spray drying). Particularly preferred is the use of hydroxypropyl methylcellulose or a cold water soluble starch. In addition, combinations of encapsulators may be used. This step creates a microdispersion which resists coalescence and maintains discrete microparticles of TPGS, phospholipid and hydrophobic phytochemical maintaining approximately a 5 micron or smaller size range. In a preferred embodiment, the microparticle is 2 microns or less. In a particularly preferred embodiment, the microparticle is 1 micron or less. Subsequently, through the process of spray drying, solvent is eliminated and the carrier (e.g., TPGS and phosphatidyl choline) is precipitated to form "microparticles" within larger starch particles. Prior to the spray drying, the mixture may be cooled to below 50° C., preferably between 15° C. and 40° C., preferably between 20° C. and 30° C., most preferably room temperature, or approximately 25° C. The amorphous, non-crystalline microparticles are easily released from the starch particles upon contact with intestinal fluids. Following this, the microparticles are compatible and coalesce with intestinal phospholipid/bile salt micelles.

Following spray drying, the solidified microparticles of co-precipitated solubilizing emulsifier, phospholipid and hydrophobic phytochemical are in an easily emulsifiable form. In the intestine, the presence of TPGS, for example, results in surfactant activity which facilitates incorporation of phytochemical-rich micelles into enterocyte lipid membranes. The intimate association of phytochemicals in microparticulate complexes with TPGS provides for advantageous uptake through the intestinal surface. Co-administered compounds specific for inhibition of the CYP 3A4 enzyme system within enterocytes can be added to the preparation in the compounding step. This "anti-CYP 3A4" component is exemplified by grapefruit concentrate or sulfophorane from broccoli, previously shown to enhance absorption of CYP 3A4 substrates by inhibiting metabolism of substances once inside enterocyte cells.

Processing of plant extracts and indole phytochemicals according to the method of the invention improves the safety and effectiveness of such chemicals when used as supplements to the diet. More consistent absorption with less inter-individual variation makes processed compounds more useful as, for example, an addition to lipid mobilizing strategies in weight loss. So far clinical study of unprocessed yohimbine has resulted in inconsistent findings of yohimbine as a promoter of weight loss (Algonkian M, et al., "Alpha-2 Adrenoceptors in Lipolysis: Alpha-2 Antagonists and Lipid-mobilizing Strategies," Am J Clin Nutrition, 55, 219S–27S (1992)).

Early studies of yohimbine without special formulation for oral absorption did not attempt to address the need for optimal pharmacokinetics of yohimbine. In addition, the timing of administration of yohimbine and control of the carbohydrate content of the diet was not considered. The effectiveness of processed yohimbe extract as described herein is enhanced in the setting of reduced carbohydrate diets favoring more active lipolysis. The sustained release characteristics of processed yohimbe extract achieved by the present invention allows for twice a day dosage resulting in a more consistent plasma level of yohimbine and its active metabolite (11-hydroxy yohimbine), which is known to have α-2 blocking activity useful for lipid mobilization. The use of the present yohimbe extract with a standardized yohimbe content but containing significant amounts of corynanthine and rauwolscine, will take advantage of the α blocking activity of the other sterioisomers providing benefits for use at a lower dose of yohimbine. Eliminating the brief, early peak in absorption seen with the use of isolated, unprocessed yohimbine reduces the potential for CNS side effects, since CNS uptake is related to peak plasma levels of indoles (LeCorre, PA, et al., "Cerebrospinal Fluid and Plasma Disposition of Yohimbine and 11-hydrox-yhohimbine in Young and Older Healthy Subjects, and Alzheimer's Disease Patients," Eur J Clin Pharmacol, 52,135–38 (1997)). Using the processed extract results in the presence of multiple active isomers in plasma at low but sustained blood levels. Thus this use of a processed natural product according to the present methods, as opposed to a pure synthetic preparation of yohimbine alone, results in greater effectiveness with less potential for side effects.

In promoting the most favorable catecholamine balance for weight loss, processed yohimbe alkaloids work in conjunction with other natural substances present in the diet. The flavonoid, epigallocatechin gallate (EGCG), found in extracts of green tea (*Camellia sinensis*), has been recently demonstrated to increase resting energy expenditure in humans (Dulloo AG, et al., "Efficacy of a Green Tea Extract Rich in ECatechin Polyphenols and Caffeine in Increasing 24-h Energy Expenditure and Fat Oxidation in Humans," Am J Clin Nutr, 70,1040–45 (1999)), and to increase the rate of weight loss in diet-restricted animals (Kao, YH, et al., "Modulation of Endocrine Systems and Food Intake by Green Tea Epigallocatechin Gallate," Endocrinology, 141, 980–87 (2000)).

EGCG is believed to be an inhibitor of catechol-0-methyl transferase (COMT), the ubiquitous enzyme responsible for the inactivation of norepinephrine and epinephrine through methylation. Thus, both processed and unprocessed yohimbe alkaloids support norepinephrine levels and interact with extracts of green tea which can slow norepinephrine metabolism. Combined use of these dietary ingredients provides the basis for methods of supporting active fat metabolism and synergistic interaction to facilitate weight loss in overweight subjects. Preferably the subjects are mammals, more preferably horses, dogs or cats, and most preferably human.

5. EXAMPLES

5.1. Example 1

INGREDIENTS OF AN ABSORPTION ENHANCING FORMULATION FOR YOHIMBE EXTRACT

Ingredient List:

1. About 30 to 60 percent by weight of a dry, powdered, ethanol based, extract from the bark of *Pausinystalia yohimbe*. The extract preferably contains 6–10 percent of yohimbine base alkaloid and 18–30 percent total alkaloids by weight. As an example, Yohimbe Powdered Extract (8%) from Kaden Biochemicals, GMBH , Hamburg, Germany, may be used.

2. About 5 to about 40 percent by weight of the following, alone or in combination: vitamin E succinate polyethylene glycol 1000; vitamin E succinate Polyethylene glycols with polyethylene glycol (with a molecular weight range of 400–2000); other polyethylene glycol esters such as those formed by fatty acids such as oleic acid or stearic acid; polyvinylpyrrolidones; polyvinylpolypyrrolidones; Poloxamer 188, Tweens; or Spans.

3. About 1 to about 20 percent by weight of the following, alone or in combination: phosphatidyl choline (derived from soy lecithin and supplied as Phospholipon 50G from Rhone Poulenc Rorer); dioleoyl phosphatidylcholine; phoshatidylglycerol; dioleoylphosphatidylglycerol; dimyristoylphosphatidylcholine; dipalmitoylphosphatidylcholine; phosphatidylethalolamines; phosphatidylserines; or sphingomyelins; or other sources of phospholipids as those from purified Milk Fat Globule Membrane; glycerolesters; poly glycerol esters; or ethoxylated castor oil.

4. About 15 to about 30 percent by weight of the following, alone or in combination: a suitable solvent, e.g., an ester solvent such as ethyl acetate or propyl acetate, but not hexanol; ethanol; butanol; heptanol; or 2-methyl-1-pentanol.

5. About 20 to about 40 percent by weight of the following, alone or in combination: modified starch such as Capsul™ Starch from National Starch, Inc.; methylcellulose; hydroxypropyl methylcellulose; hydroxyethylcellulose; hydroxypropylethylcellulose; pectin; gum arabic; gelatin; cold water soluble starch, or other polymeric matrix-forming preparation known to those skilled in the art, soluble in water and, suitable for spray drying.

6. About 0.5 to about 35 percent by weight of the following, alone or in combination: aerosil 200; or any other flow enhancing excipient from silica, or related salt, known to those skilled in the art.

5.2. Example 2
DETAILED LIST OF PRODUCTION STEPS USED FOR THE MANUFACTURE OF PROCESSED YOHIMBE 1. About 1600 grams of a yohimbe bark extract was selected.
2. The yohimbe extract was added to 1600 grams of propyl acetate solvent.
3. This mixture was heated in a 70° C. water bath and mixed thoroughly.
4. Vitamin E TPGS, 320 grams, and phosphatidyl choline, 64 grams were added to the yohimbe-propyl acetate mixture and thoroughly mixed.
5. In second heated vessel, a solution of Capsul starch containing 1200 grams of starch dissolved in 12.8 liters of deionized water was prepared with thorough mixing using a Cowles blade.
6. The mixture of yohimbe bark extract, vitamin E TPGS, phosphatidyl choline, and propyl acetate was slowly added to the second vessel containing warm starch solution and homogenized using a rotor/stator type mixer at moderate speed for 15 minutes.
7. The final homogenized mixture from the combination of the first and second vessels was cooled to room temperature and then introduced into a spray drier producing a dry flowable powdered product (processed yohimbe bark extract). A small amount of hydrophilic silica was added during spray drying to provide a free flowing powder containing the co-precipitated TPGS, phosphatidyl choline and dispersed yohimbe bark extract in an amorphous non-crystalline structure.
8. The flowable powder was collected and stored in evacuated foil sacks, after de-aerating and flushing with nitrogen.
9. Analysis of the unchanged yohimbe alkaloid revealed about 3–7 percent by weight of the yohimbine species of alkaloid.

Dispersed yohimbe extract prepared according to the process of the invention, for example, the process of Examples 1 and 2, is referred herein as "Processed Yohimbe Extract".

For effective treatment, the above preparation is administered to a mammal in an approximate dose of from 0.2 to 10 mg/kg/day by oral administration. This administration is effective in promoting the mobilization of stored fat, especially during dietary carbohydrate restriction.

Alternatively, a pure preparation of yohimbine hydrochloride (16 alpha, 17 alpha)-17-hydroxyyohimban-16-carboxylic acidmethyl ester hydrochloride) may be used in place of the yohimbe extract of Step 1. Yohimbine hydrochloride is preferably used in an amount of from 50 to 300 gms in the above recipe.

5.3. Example 3
INGREDIENTS OF AN ABSORPTION ENHANCING FORMATION FOR YOHIMBINE, CORYNANTHINE, RAUWOLSCINE AND IBOGAINE Ingredient List:
1. About 5 to about 40 percent by weight of a compound selected from the following, alone or in combination: ibogaine, yohimbine, corynanthine, and rauwolscine
2. About 5 to about 40 percent by weight of the following, alone or in combination: vitamin E succinate polyethylene glycol 1000; vitamin E succinate polyethylene glycols with polyethylene glycol (with a molecular weight range of 400–2000); other polyethylene glycol esters such as those formed by fatty acids such as oleic acid or stearic acid; polyvinylpyrrolidones; polyvinylpolypyrrolidones; Poloxamer 188, Tweens; or Spans.
3. About 1 to about 20 percent by weight of the following, alone or in combination: phosphatidyl choline (derived from soy lecithin and supplied as Phospholipon 50G from Rhone Poulenc Rorer); dioleoyl phosphatidylcholine; phoshatidylglycerol; dioleoylphosphatidylglycerol; dimyristoylphosphatidylcholine; dipalmitoylphosphatidylcholine; phosphatidylethalolamines; phosphatidylserines; or sphingomyelins; or other sources of phospholipids as those from purified Milk Fat Globule Membrane; glycerolesters; poly glycerol esters; or ethoxylated castor oil.
4. About 15 to about 30 percent by weight of the following, alone or in combination: hexanol; ethanol; butanol; heptanol; 2-methyl-1-pentanol; various ketone solvents that would be acceptable in foods such as methyl ethyl ketone, acetone and others; propylene glycol; and certain ester solvents such as ethyl acetate or propyl acetate.
5. About 20 to about 40 percent by weight of the following, alone or in combination: modified starch such as Capsul™ Starch from National Starch, Inc.; methylcellulose; hydroxypropyl methylcellulose; hydroxyethylcellulose; hydroxypropylethylcellulose; pectin; gum arabic; gelatin; or other polymeric matrix-forming preparation known to those skilled in the art, soluble in water and, suitable for spray drying.
6. About 0.5 to about 35 percent by weight of the following, alone or in combination: aerosil 200; or any other flow enhancing excipient from silica, or related salt, known to those skilled in the art.

5.4. Example 4
DETAILED LIST OF PRODUCTION STEPS USED FOR THE MANUFACTURE OF PROCESSED YOHIMBINE 1. 300 grams of the compound yohimbine was selected.
2. The yohimbine was added to 1600 grams of propyl acetate solvent.
3. This mixture was heated in a 70C water bath and mixed thoroughly.
4. Vitamin E TPGS, 320 grams, and phosphatidyl choline, 64 grams were added to the yohimbine-propyl acetate mixture and thoroughly mixed.
5. In second heated vessel, a solution of Capsul starch containing 1200 grams of starch dissolved in 12.8 liters of deionized water was prepared with thorough mixing using a Cowles blade.
6. The mixture of yohimbine bark extract, vitamin E TPGS, phosphatidyl choline, and propyl acetate was slowly added to the second vessel containing warm starch solution and homogenized using a rotor/stator type mixer at moderate speed for 15 minutes.
7. The final homogenized mixture from the combination of the first and second vessels was cooled to room temperature and then introduced into a spray drier producing a dry flowable powdered product (processed yohimbine). A small amount of hydrophilic silica was added during spray drying to provide a free flowing powder containing the co-precipitated TPGS, phosphatidyl choline and dispersed yohimbine in an amorphous non-crystalline structure.
8. The flowable powder was collected and stored in evacuated foil sacks, after de-aerating and flushing with nitrogen.

Dispersed yohimbine prepared according to the process of the invention, for example, the process of Examples 3 and 4, is referred herein as "Processed Yohimbine".

For effective treatment, the above preparation is administered to a mammal in an approximate dose of from 0.5 to 10 mg/kg/day by oral administration. This administration is effective in promoting the mobilization of stored fat, especially during dietary carbohydrate restriction.

5.5. Example 5
DEMONSTRATION OF CONTROLLED RELEASE AND ABSORPTION OF YOHIMBINE FOLLOWING ORAL ADMINISTRATION OF FORMULATED YOHIMBE EXTRACT The benefits of processing yohimbe bark extract is documented through plasma level studies in healthy volunteers in which blood levels of yohimbine are used as a marker for the absorption of the family of indole sterioisomers present in the extract (i.e., yohimbine, corynanthine and rauwolscine). The objective of these studies is to demonstrate a more prolonged half life, and a more robust area under the curve for yohimbine plasma levels.

These blood uptake studies employ a dose of 0.1 mg/kg/dose of yohimbine derived from a standard unprocessed extract containing 7% wt/wt of yohimbine alkaloids. Based on this content of yohimbine, 100 mg of extract is given for every 70 kg of body weight. Since processed yohimbe bark extract is composed of 50% standard yohimbe extract by weight, twice the mg weight of processed yohimbe extract is given to provide equal amounts of yohimbine with the mg/kg dose of processed yohimbe extract.

Plasma samples are obtained from 4 healthy middle aged male subjects studied in the fasting state. Each blood sample is obtained from an indwelling teflon cathether on a timed basis every 30 minutes for 3.5 hours. Blood is collected in heparinized collection tubes and immediately centrifuged, plasma separated and frozen. Volunteers are studied after oral dosing for three and a half hour periods with blood samples obtained every 30 minutes.

Plasma samples are extracted, derivatized and analyzed by GC-mass spectrometry to determine the presence of unmetabolized yohimbine. The gas chromataography—mass spectrometry (GCMS) system utilizes a standard curve for yohimbine based on added known amounts of a separate indole as an internal standard. Mass spectral analysis is based on application of published methods (LeVerge, R, et al., "Determination of Yohimbine and its Two Hydroxylated Metabolites in Humans by High Performance Liquid Chromatogaraphy and Mass Spectral Analysis," J of Chromatography, 574, 283–92 (1992)).

Results from Trial I—Unprocessed Standard Yohimbe Extract

Results from this trial demonstrate an early peak in yohimbine plasma levels occurring at the 30, 60 or 90 minute sample in all subjects. Following this a rapid decline to yohimbine blood levels below 10 ng/ml.

Results from Trial II—Processed Yohimbe Bark, Containing Vitamin E TPGS and Phosphatidyl Choline Results from this trial demonstrate attenuated peaks in yohimbine in comparison to Trial I when plasma levels for yohimbine are compared at the 30, 60, and 90 minute sample times. In marked contrast to the results from Trial I, a gradual increase in yohimbine plasma levels is noted for each subject with maximal peaks occurring at later time points as compared to those of Trial I.

Processed yohimbe bark is noted to result in more sustained plasma levels for yohimbine in Trial II as compared to Trial I. In each case there is a greater area under the concentration-time curve (AUC) for yohimbine demonstrated in Trial 1I as compared to Trial I.

In conclusion, results show more sustained blood levels of yohimbine in ng/ml concentration following use of processed yohimbe bark extract compared to unprocessed yohimbe bark extract. This is reflected in greater AUC determinations for absorption of yohimbine from processed yohimbe bark extract as compared to unprocessed yohimbe bark extract.

5.6. Example 6
USE OF PROCESSED YOHIMBE BARK EXTRACTS TO PROVIDE SUSTAINED APPETITE CONTROL IN HUMANS Use of processed yohimbe bark extract by volunteers results in reproducible loss of appetite for a period of hours after a single oral dose. In order to establish an advantage of the controlled release of yohimbine from processed yohimbe extract over plain yohimbe extract for appetite control, a single blind experiment is performed in 3 adult male subjects.

Published experimental work with a rapidly absorbed preparation of pure yohimbine demonstrated a dramatic reduction in daily food intake in dogs when the alkaloid was given at a daily dose of 0.4 mg/kg/day. This use of yohimbine was associated with a rapid loss of body weight (Berlan, et al., "Anorectic Effect of α-2-Antagonists in Dog: Effect of Acute and Chronic Treatment," Pharmacology Biochemistry & Behavior, 39, 313–20 (1991)). If effects on heart rate and blood pressure are to be avoided, safe dosage of yohimbine in humans should not exceed 0.1 mg per kg per dose. Therefore, a dose of 0.1 mg/kg of yohimbine from a standardized extract is chosen for the experiment. Further, since the processed yohimbe bark is 50% yohimbe extract by weight, an equivalent mg amount of yohimbine is delivered to the volunteers from the processed yohimbe bark extract by doubling the mg weight of the processed yohimbe bark dose.

Subjects are studied following a standard breakfast consisting of coffee, yogurt and fruit at 8:00 am on test days. A gelatin capsule containing either rice bran (placebo), standardized yohimbe extract, or processed yohimbe extract was given with 8 oz. of water at 10:00 AM. Only water is consumed until 6:00 PM that evening. A hunger diary is kept according to the following scale: 0=no hunger, 1=minimal hunger, 2=moderate hunger, 3=severe hunger. Each subject is studied on three occasions at least 1 week apart.

Results show a more persistent and profound appetite suppressant activity from the processed yohimbe bark extract as compared to standard yohimbe extract and placebo.

5.7. Example 7
USE OF PROCESSED YOHIMBE BARK EXTRACTS TO PROMOTE MORE ACTIVE MOBILIZATION OF FATTY ACIDS IN HUMANS Since the effectiveness of yohimbe extracts as an aid in weight loss is based in part on increased efficiency of mobilization of stored fat, it is important to compare actual levels of free fatty acids (FFA's) released following the use of unprocessed and processed yohimbe extracts. FFA's are measured in 2 healthy female subjects 4 hours following use of Yohimbe extracts, before and after 30 minutes of submaximal aerobic exercise at 50% maximum heart rate.

To control for the influence of variations in carbohydrate content of diets and body glycogen level, chosen subjects are those who had maintained a carbohydrate limited diet and who had tested positive on urine dipstick for ketones on each day of testing.

Each healthy female subject is given 1 mg/kg of unprocessed yohimbe extract on day one. Blood is obtained for FFA levels 4 hours later both before and after 30 minutes of standardized exercise on a stationary bicycle. The testing protocol is repeated 4 days later substituting processed yohimbe extract at a dose of 2 mg/kg. Again, the amount compared to unprocessed extract is doubled because the processed yohimbe bark is 50% yohimbe extract by weight. All testing is conducted following an overnight fast with standardized intake of water on the day of testing.

The results indicate a more active release of FFA's under the influence of the processed yohimbe extract than following use of the unprocessed yohimbe extract. The effects persist after submaximal exercise, indicating a greater physiologic response of fat tissue to exercise following use of the processed yohimbe extract as compared to the unprocessed yohimbe extract.

5.8. Example 8
USE OF PROCESSED YOHIMBE BARK EXTRACTS IN CONJUNCTION WITH GREEN TEA EXTRACT TO PROVIDE SYNERGISTIC DIETARY SUPPLEMENTS TO PROMOTE EFFICIENT WEIGHT LOSS IN HUMANS A clinical test of the present formulation of processed yohimbe extract is performed to demonstrate its advantage in promoting weight loss over unprocessed yohimbe extract.

To provide the optimum metabolic conditions for utilization of stored fat, this double-blind, placebo controlled, pilot study includes overweight men on a prescribed low-carbohydrate diet. Green tea extract, containing approximately 100 mg of epigallocatechin gallate (EGCG) per capsule, is also included in Groups II, V and VI. The test demonstrates amplification of weight loss by yohimbe extracts.

Previous studies of the use of yohimbe alkaloids as dietary supplements to promote weight loss in individuals on restricted diets have produced inconsistent results. These prior studies have used tableted preparations of pure yohimbine, known to have rapid absorption and a plasma half life of less than 1 hour. In one of the most successful published studies, overweight female subjects on either placebo or yohimbine (yohimbibinum hydrochloricum, Polfa Warszzawa, Poland) 5 mg 4 times per day (20 mg/day) was given for three weeks after subjects had started a weight loss diet for an initial three weeks. Significantly greater continued weight loss was observed in the yohimbine treated group along with greater energy expenditure in the treated group during exercise (Kucio, C, et al., "Does Yohimbine Act As a Slimming Drug," Israeli J Med Sci, 27, 550–6 (1991)). In a second, comparable study, a similar preparation of rapidly absorbed yohimbine (yohimbine Hcl 5.4 mg/tab, Palisades Pharmaceuticals, Tenafly, N.J., USA) was tested against placebo in a group of overweight men. An escalating dose schedule starting from 16.2 to 43.2 mg/day of yohimbine in up to three divided doses daily failed to show advantage in additional weight loss over placebo over a six month period (Sax, L, "Yohimbine Does Not Affect Fat Distribution in Men," Int. J. Obesity, 15, 561–5 (1991)).

The current protocol involves six treatment groups. They include:

I. Placebo
II. Green tea extract (700 mg/day)
III. Unprocessed yohimbe extract (150 mg/day)
IV. Processed yohimbe extract (300 mg/day)
V. Green tea extract (700 mg/day) plus unprocessed yohimbe extract (150 mg/day)
VI. Green tea extract (700 mg/day) plus processed yohimbe extract (300 mg/day)

Green tea extract (camellia sinensis) 350 mg per capsule (caffeine approximately 49 mg/capsule, total catechins above 25%), unprocessed yohimbe extract 75 mg per capsule, and processed yohimbe extract 150 mg per capsule, and placebo consisting of defatted rice bran 300 mg per capsule are all prepared in identical opaque gelatin capsules.

42 men are recruited through an advertisement in a local newspaper. All subjects are more than 20 percent over ideal body weight and less than 270 pounds in total weight. A screening evaluation excludes subjects with blood pressure above 150/90 or with a high score on the Tyrer anxiety scale (Tyrer, P., et al., "The Brief Scale for Anxiety: A Subdividvision of the Comprehensive Psychopathological Rating Scale," J. Neurol. Neurosurg. Psych., 47, 970–5 (1984)).

Patients are randomly assigned to Group I, II, III, IV, V or VI. For the first two weeks all participants begin the same intervention level diet as specified in "The Protein Power Lifeplan, M. R. Eades, and M. D. Eades, Warner Books, 2000, under the "Purist Plan." This diet limits individual to approximately 100 gms of low-glycemic carbohydrates per day. Treatment with capsules begins at the start of week 3 and continues through the end of week 6. One capsule from bottle "A" (green tea or placebo) and one capsule from bottle "B" (placebo, unprocessed yohimbe extract, or processed yohimbe extract) are taken twice a day at 10 AM and at 3 PM. All patients maintain a "Hunger Diary" assessing level of hunger before retiring each night according to the following scale: 0=no hunger, 1=minimal hunger, 2=moderate hunger, 3=severe hunger.

Patients are weighed on a registered scale at three time points: enrollment (Time 1), start of capsules (Time 2), and completion of 4 weeks of Capsules (Time 3).

The results indicate a greater average weight loss for Group VI, who are treated with the processed yohimbe extract in combination with green tea extract. At exit interviews, patients in Group VI rated their evening hunger score less than those in the other groups. The results of this study provide support for processed yohimbe extract offering an advantage over unprocessed yohimbe extract when used during a low-carbohydrate weight-loss plan in conjunction with green tea extract. In addition, the results show a synergistic action between green tea extract and yohimbe, regardless of whether the yohimbe is processed according to the invention or not, even though the amount of weight loss is greatest when the processed yohimbe is used.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A process for the preparation of a composition comprising the steps of:
   a. heating one or more solubilizing emulsifiers selected from the group consisting of vitamin E succinate polyethylene glycol 1000, polyvinylpyrrolidone, polyoxyethylene stearate, sodium cholate, deoxycholate and taurocholate;
   b. adding to the product of step (a) a solvent and a surfactant phospholipid selected from the group consisting of phosphatidyl choline, dioleoyl phosphatidyl choline, phosphatidylglycerol, dioleoylphosphatidylglycerol, dimyristoylphosphatidylcholine, dipalitoylphosphatidylcholine, phosphatidylethanolamine, phosphatidylserine and sphingomyelin to produce a solution;
   c. dissolving in the solution of step (b) one or more phytochemicals or compositions comprising phytochemicals selected from the group consisting of *Pausinystalia yohinbe* bark extracts, *Tabernanthe iboga* extracts, yohimbine, ibogaine, corynanthine, and rauwolscine;
   d. adding to the solution of step (c) a solution containing an encapsulator;
   e. mixing the solution produced in step (d) to produce a microdispersion with a particle size of 5 microns or less; and
   f. spray drying the resulting mixture to leave a solid hydrophobic phytochemical composition.

2. The process of claim 1 wherein said encapsulator is selected from the group consisting of starch and gelatin.

3. The process of claim 1 wherein said solvent is selected from the group consisting of hexanol, ethanol, butanol, heptanol, 2-methyl-1-pentanol, methyl ethyl ketone, acetone, propylene glycol, and ethyl acetate.

4. The process of claim 1 wherein said composition comprising phytochemicals is *Pausinystalia yohimbe* bark extract, and said solvent is selected from the group consisting of propyl acetate and ethyl acetate.

5. The process of claim 1 wherein said particle size is 3 microns or less.

6. The process of claim 1 wherein said particle size is 2 microns or less.

7. A composition prepared according to the process of claim 1.

8. A composition prepared according to the process of claim 3.

9. A composition prepared according to the process of claim 4.

10. The composition of claim 8 further comprising green tea extract.

* * * * *